US010265149B2

(12) United States Patent
Jaisson (10) Patent No.: US 10,265,149 B2
(45) Date of Patent: Apr. 23, 2019

(54) METHOD AND SYSTEM FOR MODELING THE MANDIBULAR KINEMATICS OF A PATIENT (71) Applicant: MODJAW, Ste Helene du Lac (FR)

(72) Inventor: Maxime Jaisson, Les Marches (FR)

(73) Assignee: MODJAW, Ste Helene Du Lac (FR)

( * ) Notice: Subject to any disclaimer, the term of this patent is extended or adjusted under 35 U.S.C. 154(b) by 0 days.

(21) Appl. No.: 15/520,409

(22) PCT Filed: Oct. 20, 2015

(86) PCT No.: PCT/FR2015/052816
§ 371 (c)(1),
(2) Date: Apr. 19, 2017

(87) PCT Pub. No.: WO2016/062962
PCT Pub. Date: Apr. 28, 2016

(65) Prior Publication Data
US 2017/0312064 A1 Nov. 2, 2017

(30) Foreign Application Priority Data
Oct. 20, 2014 (FR) ..................... 14 60071

(51) Int. Cl.
G06K 9/00 (2006.01)
A61C 19/045 (2006.01)
(Continued)

(52) U.S. Cl.
CPC .............. A61C 19/045 (2013.01); A61B 1/24 (2013.01); A61B 5/0077 (2013.01);
(Continued)

(58) Field of Classification Search
CPC ....... A61C 19/045; A61B 1/24; A61B 5/0077; A61B 5/1079; A61B 5/1127
See application file for complete search history.

(56) References Cited

U.S. PATENT DOCUMENTS 9,922,454 B2 * 3/2018 Jaisson .................. G06T 17/10
2002/0015934 A1 2/2002 Rubbert et al.
(Continued)

FOREIGN PATENT DOCUMENTS

WO WO-2013030511 3/2013

OTHER PUBLICATIONS

K. T. Rajamani, S. C. Joshi and M. A. Styner, "Bone model morphing for enhanced surgical visualization," 2004 2nd IEEE International Symposium on Biomedical Imaging: Nano to Macro (IEEE Cat No. 04EX821), 2004, pp. 1255-1258 vol. 2.doi: 10.1109/ISBI.2004.1398773 (Year: 2004).*

(Continued)

Primary Examiner — Wesley J Tucker
(74) Attorney, Agent, or Firm — Womble Bond Dickinson (US) LLP (57) ABSTRACT The invention relates to a method for modeling the mandibular kinematics of a patient, comprising:
acquiring at least one stereoscopic image of the face of the patient by means of a stereoscopic camera,
constructing, from said stereoscopic image, a three-dimensional surface model of the face of the patient,
identifying characteristic elements of the face of the patient on said stereoscopic image or on said three-dimensional surface model of the face of the patient,
from said characteristic elements, determining, on said stereoscopic image, respectively said three-dimensional surface model of the face of the patient, reference points, axes and planes of the face of the patient,
obtaining a three-dimensional model of the maxillary dental arch and a three-dimensional model of the mandibular dental arch of the patient,
registering the three-dimensional models of the dental arches with respect to the reference planes of the three-dimensional surface model of the patient,
(Continued)

recording the mandibular kinematics of the patient, applying said recorded mandibular kinematics to the three-dimensional models of the registered dental arches, so as to animate said three-dimensional models.

17 Claims, 9 Drawing Sheets (51) Int. Cl.
    A61B 5/107    (2006.01)
    G06T 19/00    (2011.01)
    A61B 1/24     (2006.01)
    A61B 5/00     (2006.01)
    A61B 5/11     (2006.01)
    A61B 6/14     (2006.01)
    A61B 8/08     (2006.01)
    A61C 13/34    (2006.01)
    G06T 15/10    (2011.01)
    A61C 9/00     (2006.01)

(52) U.S. Cl.
    CPC .......... *A61B 5/1079* (2013.01); *A61B 5/1127* (2013.01); *A61B 6/14* (2013.01); *A61B 8/0875* (2013.01); *A61C 13/34* (2013.01); *G06T 15/10* (2013.01); *G06T 19/00* (2013.01); *A61C 9/008* (2013.01); *G06K 9/00288* (2013.01); *G06T 2210/41* (2013.01); *G06T 2215/16* (2013.01)

(56) References Cited

U.S. PATENT DOCUMENTS

| | | | | |
|---|---|---|---|---|
| 2004/0015327 A1* | 1/2004 | Sachdeva | ................. | A61C 7/00 702/167 |
| 2008/0176182 A1* | 7/2008 | Hultgren | ................ | A61C 11/00 433/69 |
| 2008/0182220 A1* | 7/2008 | Chishti | .................... | A61C 7/00 433/24 |
| 2009/0068617 A1 | 3/2009 | Lauren | | |
| 2009/0311647 A1* | 12/2009 | Fang | .................... | A61C 19/045 433/24 |
| 2012/0015316 A1 | 1/2012 | Sachdeva et al. | | |
| 2013/0235163 A1 | 9/2013 | Joo | | |
| 2013/0329020 A1* | 12/2013 | Kriveshko | ......... | A61B 1/00009 348/50 |
| 2014/0272764 A1* | 9/2014 | Miller | .................. | A61B 1/0684 433/27 |
| 2014/0294273 A1* | 10/2014 | Jaisson | ................ | A61B 5/7425 382/131 |
| 2015/0238287 A1* | 8/2015 | Pulido | ................ | A61B 1/00147 356/601 |
| 2016/0128624 A1* | 5/2016 | Matt | ..................... | A61C 19/045 600/301 |
| 2018/0104036 A1* | 4/2018 | Jaisson | .................. | A61C 19/05 |

OTHER PUBLICATIONS

MODJAW, "French Preliminary Search Report," FR Application No. 1460071 (dated Jun. 30, 2015) (with English translation cover sheet).

MODJAW, "International Search Report and Written Opinion," PCT Application No. PCT/FR2015/052816 (dated Jan. 27, 2016) (with English translation cover sheet).

Furtado, et al.; A specialized motion capture system for real-time analysis of mandibular movements using infrared cameras; BoMedical Engineering Online 2013; http://www.biomedical-engineering-online.com/content/12/1/17.

Sedky Adly, et al.; Recording and Measuring of Jaw Movements using a Computer Vision System; International Journal of Computer Applications (0975-8887) vol. 81-No. 18, Nov. 2013.

* cited by examiner

METHOD AND SYSTEM FOR MODELING THE MANDIBULAR KINEMATICS OF A PATIENT

FIELD OF THE INVENTION

The present invention relates to a method for modeling the mandibular kinematics of a patient, as well as a system for the implementation of said method.

BACKGROUND OF THE INVENTION

When the dental organ is damaged, the role of the dental surgeon is to restore it.

When there is significant decay, this restoration calls upon prosthetic devices that replace all or part of one or more of the teeth concerned.

This cannot be done without taking into consideration dental occlusion, which is the manner in which interdental and interarch contacts are organized.

In this context, the management of interdental contacts is a therapeutic imperative.

Furthermore, other situations exist in which the management of dental contacts is a therapeutic imperative.

For example, when the teeth are in ectopic position, an orthodontic treatment is undertaken in such a way as to displace the teeth thanks to an apparatus. The configuration and the distribution of the occlusal contacts change and rules need to be respected in this case so as not to harm the patient.

In other cases, when disorders of the joint or muscular contraction are diagnosed and have a relation with occlusion, the dental surgeon may, through the design of an occlusal mouth guard, attenuate or even correct these dysfunctions.

By extension, occlusion ensures the interface between the two maxillaries. Their confrontation is possible thanks to a moveable bone: the mandible (lower maxillary).

The quality of this occlusion is vital and has to assure three essential functions (centering; bracing; guiding) of this same mandible in order to preserve the surrounding structures (joint, muscles, etc.).

The motility of the mandible is due to a joint, the temporomandibular joint (TMJ) and a setting in motion by the contraction of the mastication muscles.

At all times, the dental surgeon is concerned with preserving the good health of these components but also its re-establishment when pathologies are objectivized (such as myalgia, arthropathy). In this case, the dental surgeon may, through rehabilitation of the occlusion, have a retroactive effect on pathologies of the manducatory apparatus.

The construction or reconstruction of the occlusion is under the influence of certain determinants, which are data linked to the patient having an influence on the occlusal anatomy.

These determinants are important to apprehend in certain situations because the prosthesis technician, by managing them, draws inspiration from them to model the occlusal surface of the teeth.

The determinants of occlusion are factors that influence occlusion. These factors are divided into two groups: fixed determinants and determinants capable of being modified by remodeling or repositioning of the teeth.

Modifiable determinants are:
  the shape of the teeth (height of the cusps, depth of the fossa, etc.)
  the position of the teeth,
  the vertical dimension,
  the occlusal curves.

Fixed determinants are:
  (1) the vertical and horizontal positioning of the arches with respect to the posterior determinant,
  (2) the condylar spacing
  (3) the anteroposterior positioning of the arches with respect to the articular posterior determinant,
  (4) the articular posterior determinant, which is defined by:
    the condylar slope
    the Bennett angle
    the initial Bennett movement.

These fixed and modifiable determinants are interdependent of each other.

The modifiable determinants are those on which the dental surgeon concentrates his/her diagnosis and rehabilitation work. To perfect the diagnosis and thereby ensure optimum rehabilitation for the patient, a study of the fixed determinants and the interdependences between the fixed and modifiable determinants is necessary.

To this end, there exists on the market tools known as articulators which simulate more or less well the physiology of the manducatory apparatus.

These articulators are commercially available in mechanical or digital form. These simulators reproduce mandibular kinematics making it possible to take into account the fixed determinants in the diagnostic analysis. The parameterization of these simulators is carried out by using approximations of the fixed determinants 2, 3 and 4. The anatomy of the temporomandibular joint is simulated thanks to an addition of angular values schematizing the courses of the mandibular condyle in space. This is parameterized mechanically at the level of the condylar boxes of the simulator.

However, due to their design and their mode of operation, the simulators are a source of errors. In addition, they only enable an approximate management of the determinants, and at the price of tedious programming and costly handling at the dental surgery. Moreover, the mandibular kinematics recreated from these simulators are only an approximate reproduction of the real mandibular movements.

A direct consequence is the outsourcing to a prosthetist of this task, which is nevertheless decisive because it guarantees a prosthetic treatment that is reliable, comfortable and durable.

Document WO 2013/030511 describes a method for designing a dental appliance that implements a recording of the mandibular kinematics of the patient.

This method firstly comprises either obtaining a volumetric image of the facial skeleton by a tomodensitometry technique, or determining reference planes of the facial skeleton by pinpointing points of interest on the face of the patient.

Furthermore, three-dimensional models of the dental arches of the patient are obtained. Said models, positioned with respect to each other during their creation, are registered with the volumetric image of the facial skeleton or the reference planes determined beforehand.

Recording the mandibular kinematics is implemented by equipping the patient with a marker fixed on the forehead of the patient and markers fixed directly on the teeth of the mandibular arch or on the mandible through the intermediary of a support, and by detecting and recording the displacements of said markers by means of a camera during mandibular movements of the patient.

However obtaining elements making it possible to position the models of the dental arches with respect to each other still needs to be improved. In fact, tomodensitometry assumes exposing the patient to X-rays and it is sought to minimize exposure of the patient to such rays.

With regard to the alternative solution consisting in determining the reference planes of the facial skeleton, it requires a certain number of manipulations by the practitioner to point at the different points of interest.

BRIEF DESCRIPTION OF THE INVENTION

An aim of the invention is to propose a method for modeling the mandibular kinematics of a patient guaranteeing management of the fixed determinants in order to control their characteristics and their incidences on the modifiable determinants, this method having to be easier to implement than known methods.

As will be seen in detail hereafter, this method comprises among others a veritable recording of the mandibular kinematics which, once modeled thanks to software, makes it possible to animate digital models of the dental arches of the patient. The taking into account of the determinants is done in a simple and intuitive manner.

Moreover, the information provided by the software and hardware aspects of the invention is much more exhaustive and is a real representation of the morphological and morphodynamic data of the patient.

The method offers the advantage of being conducted in real time in the practitioner's surgery, thereby ensuring a complete and customized study of the patient.

The information made available includes the position of the dental arches in space with respect to the joints and to the facial skeleton. Its interest is to study (in the case of occlusal analysis) and to reconstruct the occlusal curves. These curves, the SPEE curve and the WILSON curve, qualify the intraarch organization. In a simplified manner, these curves correspond to the manner in which the occlusal surfaces of the teeth, their cusps and the incisal edges are oriented in space. This provides knowledge on the possibilities of distribution of forces and interarch meeting. This leads to an analysis on the individual shape of each tooth, its specific anatomy, the depth of the depressions, the cusp height, its specific position with respect to other neighboring and antagonistic teeth.

In accordance with the invention, a method for modeling the mandibular kinematics of a patient is proposed, comprising:
    acquiring at least one stereoscopic image of the face of the patient by means of a stereoscopic camera,
    constructing, from said stereoscopic image, a three-dimensional surface model of the face of the patient,
    identifying characteristic elements of the face of the patient on said stereoscopic image or on said three-dimensional surface model of the face of the patient,
    from said characteristic elements, determining, on said stereoscopic image, respectively said three-dimensional surface model of the face of the patient, reference points, axes and planes of the face of the patient,
    obtaining a three-dimensional model of the maxillary dental arch and a three-dimensional model of the mandibular dental arch of the patient,
    registering the three-dimensional models of the dental arches with respect to the reference planes of the three-dimensional surface model of the patient,
    recording the mandibular kinematics of the patient,
    applying said recorded mandibular kinematics to the three-dimensional models of the registered dental arches, so as to animate said three-dimensional models.

According to one embodiment, the stereoscopic image of the face of the patient is a color image and a texture based on said image is applied to the three-dimensional surface model.

According to another embodiment, the stereoscopic image of the face of the patient is a black and white image of the face of the patient and, after constructing the three-dimensional surface model from said image, a color image of the face of the patient is imported and a texture is applied to said model from said imported color image.

Advantageously, the method comprises the display in real time, on a screen, of a video image of the face of the patient acquired by the stereoscopic camera and reference axes and planes of the face of said patient.

According to one embodiment, the step of registering the three-dimensional models of the dental arches with respect to the reference planes of the patient comprises:
    generating a plurality of points on the dental arches in the three-dimensional surface model of the face,
    pointing said points in the mouth of the patient by means of a pointer bearing markers detectable by the stereoscopic camera,
    detecting said markers by the stereoscopic camera while pointing each point and determining each point in the frame of reference of the camera,
    matching the points between the frame of reference of the camera and the three-dimensional surface model.

Preferably, while pointing the points in the mouth of the patient, the head of the patient is equipped with a plurality of markers visible by the stereoscopic camera.

Alternatively, the step of registering the three-dimensional models of the dental arches with the three-dimensional surface model of the face comprises:
    obtaining a stereoscopic image of the face of the patient on which appear at least three teeth of the maxillary dental arch of the patient,
    detecting said teeth by a facial recognition method,
    matching said teeth on the three-dimensional surface model of the patient and on the model of the maxillary dental arch.

Optionally, the method further comprises constructing a three-dimensional model of the bone structure of the face of the patient.

Said construction may be carried out from a tomodensitometric image of the head of the patient. Alternatively, said construction is carried out from an ultrasound image of the bones of the mandible and the maxillary. Alternatively, said construction is carried out by a "BONE MORPHING" technique from the three-dimensional surface model of the face of the patient.

In a particularly advantageous manner, to record the mandibular kinematics of the patient, a set of markers detectable by the stereoscopic camera is fixed on the head of the patient and said mandibular kinematics are recorded by means of said stereoscopic camera.

According to one embodiment, the stereoscopic camera comprises infrared emitters and/or a structured light projector.

The invention also relates to a system for modeling the mandibular kinematics of a patient, comprising:
    a processor,
    a memory coupled to the processor,
    a display screen coupled to the processor for displaying data calculated by the processor,
    a stereoscopic camera coupled to the processor to provide stereoscopic images of the face of the patient, a set of markers detectable by the stereoscopic camera, comprising a device for fixing said set on the head of the patient, such as a headset.

BRIEF DESCRIPTION OF THE DRAWINGS

Other characteristics and advantages of the invention will become clear from the detailed description that follows, with reference to the appended drawings in which.

DETAILED DESCRIPTION OF THE INVENTION

The method for modeling the mandibular kinematics of a patient mainly comprises the following steps:
  3D surface modeling of the face by acquisition by means of a stereoscopic camera and reconstruction, the reconstruction being able to be carried out according to different embodiments, notably:
    stereoscopic reconstruction, derived from photogrammetry,
    reconstruction from structured light projected onto the face using a video-projector,
    modeling from a laser beam projected onto the face of the patient,
  placement of reference points, axes and planes of the face, implementing a facial recognition method;
  positioning the dental arches with respect to these planes, said planes being associated or not with the 3D surface model of the face (determination of the fixed determinants 1 and 3);
  recording and studying the mandibular kinematics (determination of the determinant 4);
  potentially, incorporating the bone structures.

This method is implemented by computer.

The system enabling the implementation of the method comprises:
  a stereoscopic camera, potentially equipped with an infra-red emitter, a video-projector or a laser projector;
  a set of markers detectable by the stereoscopic camera, comprising a device for fixing said set to the head of the patient (for example, this set is in the form of a headset intended to be fastened onto the forehead of the patient),
  a computer coupled to the camera, comprising a processor for operating algorithms for processing images and modeling described below,
  a memory to record the images acquired and the models used,
  a display screen to enable the practitioner to visualize the different steps implemented in the course of the method.

3D Modelling of the Face of the Patient

Case 1: By Stereoscopic Acquisition

This modeling implements a stereoscopic camera for acquiring an image of the face of the patient. Thanks to computer processing of the stereoscopic image, a three-dimensional reconstruction of the face of the patient is obtained.

Furthermore, if the stereoscopic camera is in color, the 3D model may be textured automatically. If the camera is in black and white, the texture may be obtained thanks to a color photograph imported at a later stage at the software level. Correlation points are chosen between the image and the model so as next to place the photograph over the model by distributing colorimetric information.

In order to re-transcribe human vision, a stereoscopic camera uses two sensors and two objectives to simulate the eyes. The reconstruction software next seeks, in the two images, the object looked at in order to calculate the angles of convergence. The stereoscopic camera used is a pre-calibrated camera. The process of rectification consists in replacing each pixel of the image at its theoretical place thus making it possible to compensate for alignment defects of the sensors, as well as the different effects and distortions of the optics. The new position of each pixel is obtained by calibrating the camera when it is being focused. The calibration consists in presenting to the two cameras images comprising perfectly identifiable horizontal and vertical lines. The software searches for the lines and the line intersections in each image pair. It next displaces each pixel of each image so that the intersections of points are the most aligned possible and correspond line by line between the left camera and the right camera. This calculation is automated by the calibration software.

Figure 1:
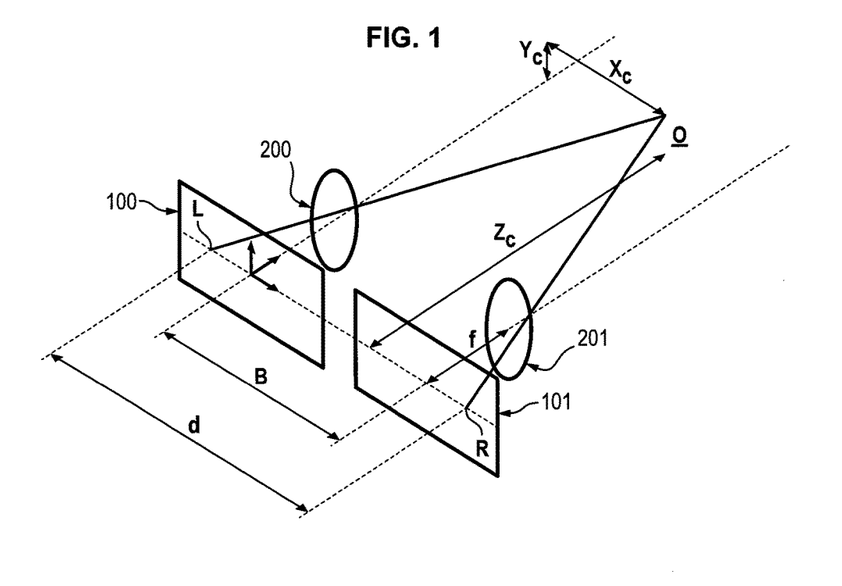
FIG. 1 is a schematic diagram of a stereoscopic acquisition.

FIG. 1 illustrates two sensors 100, 101, assumed perfect, perfectly aligned, in a plane looking at an object O through perfect objectives 200, 201.

The distance d that separates the object O on the two images corresponds to the human angle of convergence. Furthermore, it is possible to calculate the distance Zc between the sensors 100, 101 and the object O by the following calculation:

$$Zc = \frac{B*f}{(L-R)} = \frac{B*f}{d}$$

with:
B: the inter orbital distance,
f: the focal distance, and
L and R the respective position of the object in each image.
(Xi, Yi) designate the position of the object in the left image, and (Xc, Yc, Zc) the position of the object in the left camera plane.

Figure 2:
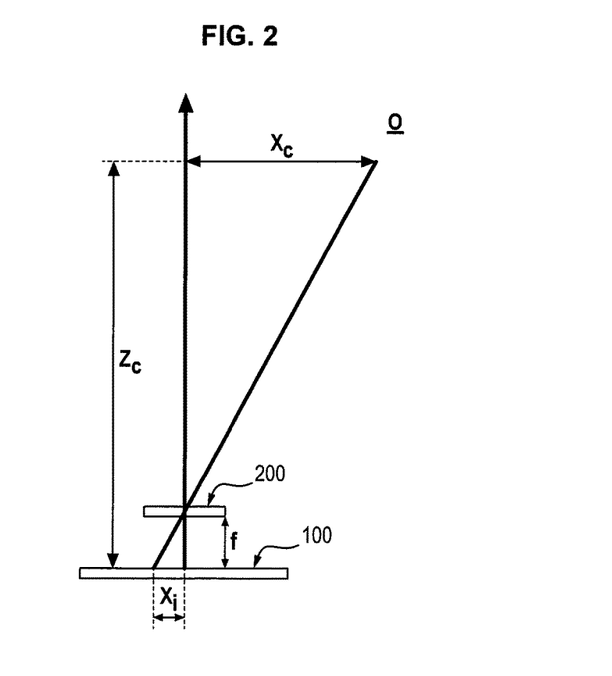
FIG. 2 is a schematic diagram in top view of the sensor/lens/object assembly during a stereoscopic acquisition.

FIG. 2 is a diagram in top view of the sensor 100/objective 200/object O assembly.

It is possible to write:

$$\frac{Xi}{Xc} = \frac{f}{Zc}$$

Xc may thus be calculated as a function of Xi, Zc and f:

$$Xc = \frac{Xi * Zc}{f}$$

In the same way, Yc is expressed as follows:

$$Yc = \frac{Yi * Zc}{f}$$

The position (Xc, Yc, Zc) of the object O is thus entirely known.

To calculate a depth map, it is then necessary to identify which pixel of the right image corresponds to which pixel of the left image.

To do so, several methods exist.

The simplest method is to search for each left image which pixel of the right image has the same value. In order to limit error, the algorithm takes into account not only the pixel in itself but also the eight surrounding pixels. This method is called the sum of absolute differences (SAD). This method is conventionally used to find a pattern in an image. Its main drawback is its great sensitivity to variations in luminosity. If for example the left image is more luminous than the right image, it will be difficult to find pixels with exactly the same value. This solution is all the same very widespread because it is simple to put in place. It is rather recommended for controlled interior lightings.

An alternative is to transform the image so as to only keep light variations from one pixel to the other and no longer the real value. The algorithm conventionally used is called the Census transform. It makes it possible to obtain two identical images, even if they have not been taken with exactly the same light conditions. Next, it is necessary to search for each pixel of the left image which pixel of the right image has the same value. This algorithm is called the Hamming distance calculation.

Once which pixel of the left image corresponds to which pixel of the right image has been identified, it is possible to create the depth map. An image is thus created of which the value of each pixel corresponds to the distance in number of pixels between the left pixel and its correspondent in the right image.

In this case and for the present invention, it is possible to produce stereoscopic acquisitions of the face and to recover therefrom a surface meshing. An automatic registering algorithm is used to associate the meshings in so far as the acquisitions have been made along different viewing angles (facing, profile, ¾, etc.).

This meshing forms the 3D model of the face of the patient that is used in the remainder of the method.

To facilitate the registering, the stereoscopic camera may be equipped with additional electronic components such as gyroscopes, accelerometers, inertial sensors. In the case where the camera is moved around the face of the patient, a movement information is provided to the software to determine the viewing angle with respect to the initial image and thus facilitate the association of the surfaces with each other.

Case 2: By Projection of Structured Light

To this end, a series of light patterns (lines, squares, circles, etc.) is projected onto the face of the subject by means of a video-projector, creating deformed images of these patterns on the face of the patient. As a function of the distance to the surface, the patterns take different shapes on account of the offset positioning of the projector and the stereoscopic camera. Next, software deduces therefrom the shape of the face as a function of the set of deformed surfaces that it has at its disposal and the distance between the points constituting said pattern.

Case 3: By Laser Projection and Scanning

To this end, several laser bands are projected while scanning onto the face of the subject which are also seen by the objectives of the stereoscopic camera for situating each point. As a function of the distance to a surface, the point appears at a different spot in the field of vision of the different objectives. This technique is called triangulation because each point of the laser bands, the objective and the laser emitter form a triangle. The length of a side of said triangle, namely the distance between the objective and the laser emitter is known. The angle of the side of the laser emitter is also known. The angle of the side of the objective may be determined by looking at the emplacement of the laser point in the field of vision of the camera. These three data determine the shape and the dimensions of the triangle and give the position of each point of the laser bands.

Determination of Reference Planes of the Face by Facial Recognition

In order to place the reference points, axes and planes of the face, resort is made to automatic detection algorithms applied to the 3D model determined previously or to an image (black and white or color) of the face of the patient.

The reference points have the interest of characterizing the morphology of the face of the patient in order to guide the diagnosis and to give architectural references for the modeling and the implementation of the treatment.

Figure 3A:
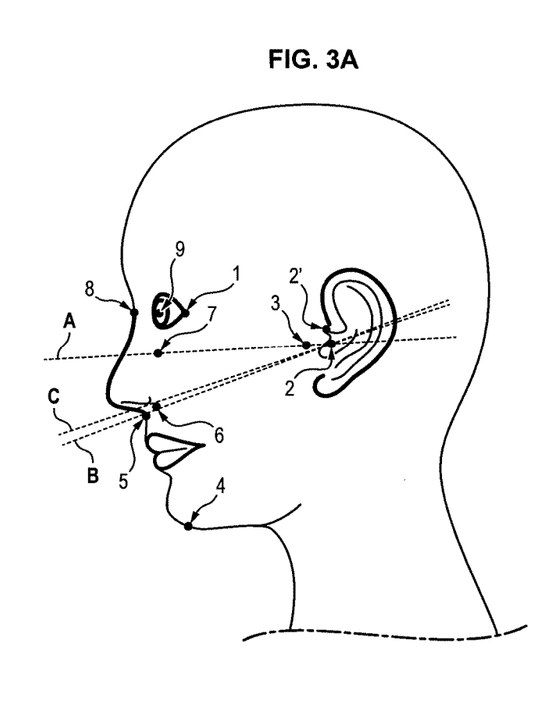
FIGS. 3A and 3B show a part of the reference points, axes and planes, represented on a 3D model of the face of the patient.
Figure 3B:
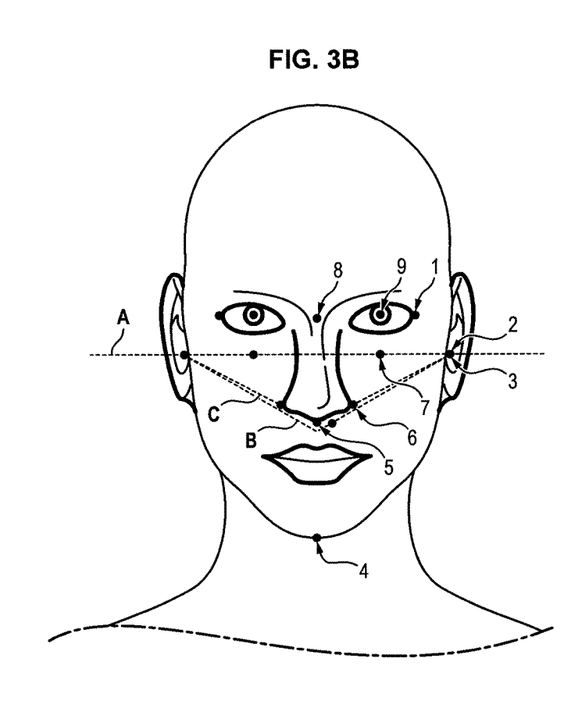

With reference to FIGS. 3A and 3B, the reference points are the following:

1. Ectocanthion: lateral angle of the eye, where the eyelids join.
2. Tragion: highest point of the tragus of the ear in the sagittal plane.
2'. Summit of the angle of the tragus.
3. Condylar point or point of emergence of the hinge axis (one right, one left); as indicated below, several definitions of this point are possible.
4. Chin: lowest point of the cutaneous chin.
5. Sub-nasal point: at the base of the nose, the highest and the most set-back point of the nasolabial fold.
6. Ala of the nose: junction point between the ala of the nose and the upper lip (one right, one left).
7. Infra-orbital point: point the most inclined of the lower edge of the orbit (one right, one left).
8. Cutaneous nasion: point of the saddle nose; in the sagittal plane, it is, on the cutaneous profile, the point the most set-back of the frontonasal fold.
9. Pupillary point: Point situated at the center of the pupil (one right, one left).

This list is not exhaustive and may be enriched by the user.

All of these points may be placed on the representation of the face of the patient in different ways which are described below.

These points are gathered together to generate the reference planes and axes namely:

A. Axis-orbital plane: Plane going through the condylar point and the infra-orbital plane.

B. Camper plane: Plane going through the tragion and the sub-nasal point.

C. Wing plane of the tragion nose.

Other reference planes and axes, not referenced in FIGS. 3A and 3B, are:
- the median sagittal plane going through the nasion, the sub-nasal point and the point situated at equidistance from the condylar points.
- bicondylar axis: the axis going through the left condylar point and the right condylar point.
- the bi-pupillary axis: the axis going through the left and right pupillary points.

The set of these points is placed either on the 3D surface model of the patient if this has been constructed beforehand, or on a stereoscopic image of the face of the patient in black and white or in color, constructing the 3D model of the face of the patient being carried out next. Three embodiments are described hereafter.

Case 1: From the 3D Acquisition of the Face of the Patient

This embodiment uses a 3D surface modeling of the face of the patient obtained thanks to the stereoscopic reconstruction method described above.

On the 3D surface model obtained, it is possible to place over and deform a model gathering together the contours of the different characteristic elements of the face to encompass the eyes, the mouth, the ears and the nose.

The deformation takes place whatever the orientation of the model in space (facing, profile, etc.).

Figure 4:
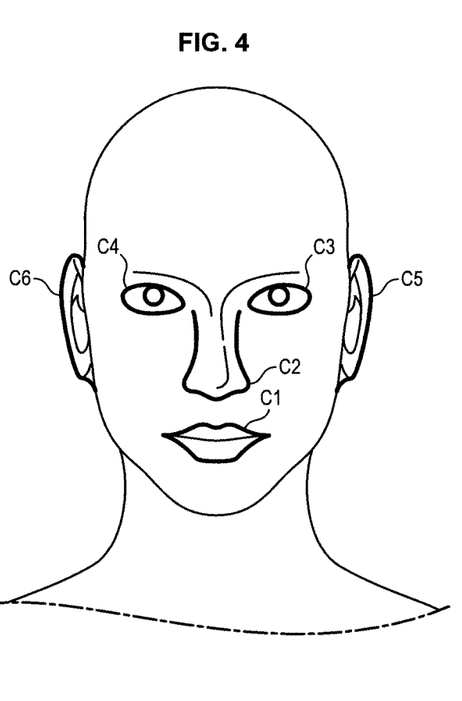
FIG. 4 illustrates the placement of contours of the characteristic elements of the face (nose, mouth, ears, eyes) on the 3D surface model of the face of the patient.

These contours C1, C2, C3, C4, C5, C6 are not necessarily displaced as in FIG. 4, but they are, whatever the case, associated with the meshing to facilitate the detection of the reference points.

The positioning of the reference points, axes and planes is then applied by the software to the 3D surface model, using the emplacement of the characteristic elements of the face.

Case 2: From Black and White Images

The stereoscopic camera is composed of two objectives that can supply black and white images.

Firstly, a photo or video of the face is taken.

Then the software analyses different aspects of this image to highlight the individual characteristics specific to the face for which it is programmed (the eyes, the position of the nose, the shape of the chin, the ear, etc.). The reference points described above are next placed using these marks. The stereoscopic method next determines the position of each point in space.

This method calls on several techniques including the so-called Eigenface technique. Firstly, the image of the face is broken down by the software into several images using levels of gray. Each of these images then highlights a particular characteristic. This technique is associated with the technique of the analysis of characteristics adding to each of the images the position and the distance between the points based on the analysis of luminosity variations of the anatomical elements of the face (nose, eye, ear, mouth). This analysis is done for example facing, profile and ¾. A deformable model is applied to the different images.

Case 3: From Color Images

The same method as in case 2 may be applied to color images. The software breaks down the color images into shades of gray. This is the case when color cameras are used.

The use of the distribution of the RGB (red green blue) color pixels makes it possible to refine the application of the deformable model on the image and does so in the three planes of space enabled by the stereoscopy.

Once the reference planes, axes, and points have been found and validated, their position is next locked-in in the mark of the headset fixed on the head of the patient.

Determination of the Condylar Point

The condylar point 3 cannot be obtained directly because it does not correspond to a characteristic element visible on an image or a model of the face.

The situation in space of this point may be done on the 3D model of the face obtained by 3D reconstruction or on the 2D images derived from the objectives of the stereoscopic camera, from other reference points determined beforehand.

Figure 5:
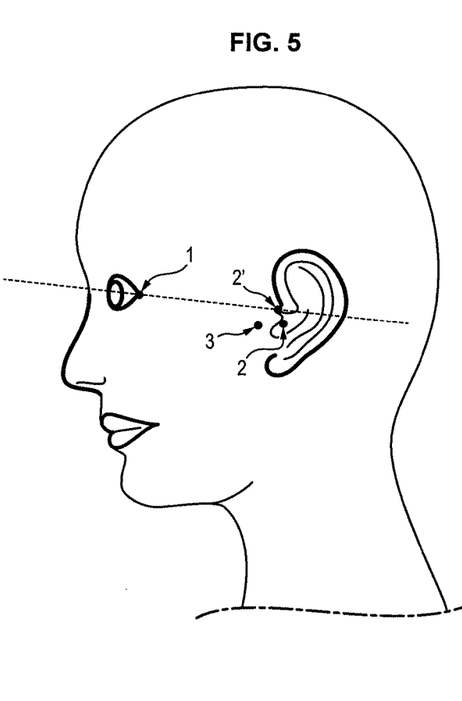
FIG. 5 shows the principle for determining the condylar point on the 3D surface model of the face of the patient.

As illustrated in FIG. 5, the positioning of the condylar point 3 depends on the situation of two other points: the ectocanthion 1 and the summit 2' of the angle of the tragus. By convention, the condylar point 3 is situated 10 mm in front of and 5 mm below the line connecting the summit of the angle of the tragus to the ectocanthion.

Another method for determining the condylar point, implementing mandibular kinematics, will be described hereafter.

Association of Augmented Reality

Optionally, once the calculation is performed by the software to place the points and the characteristic elements, these may be displayed in real time on the screen thanks to the video of the stereoscopic camera.

The face of the patient is displayed on the screen surmounted by the reference planes and axes without having need to place the frontal headset on the patient.

Determination of the positioning of the dental arches with respect to the facial skeleton and to the bicondylar axis This technique replaces the use of the mechanical tool called facebow.

The objective is to reproduce in a digital manner the veritable positioning of the arches of the patient with respect to the bone mass.

The method thus consists in using the different aforementioned technologies in order to place the digitized maxillary and mandibular models with respect to the reference planes and points characterizing the facial skeleton. Orientation and position of the models of the dental arches are thereby obtained.

Two embodiments enabling the positioning of the dental arches are described below.

Case 1: Pointing of Points on the Dental Arch of the Patient

Figure 6A:
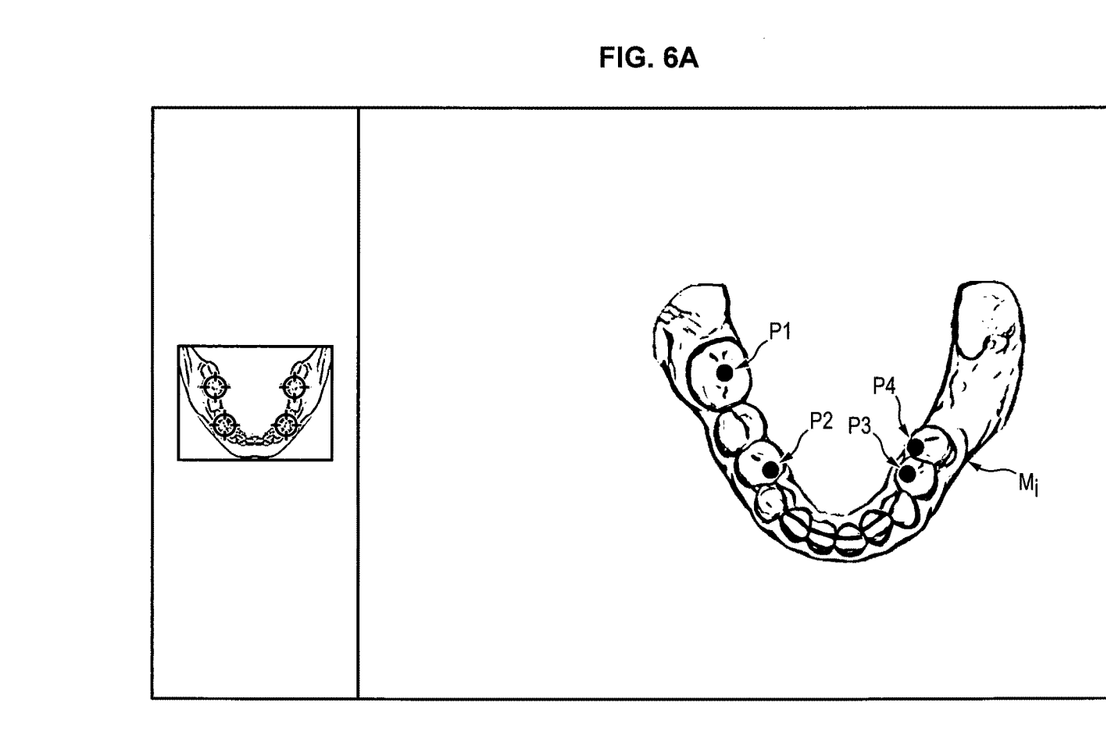
FIGS. 6A and 6B illustrate the principle of pointing enabling the registering of the dental arches with the 3D model of the face of the patient.

The points to search for are placed in a random manner on the 3D model of the dental arches, whether the arch is partially toothed, whether it has prepared teeth or implanted abutments or whether the arch is gap-toothed (cf. FIG. 6A, where four points P1, P2, P3 and P4 may be seen on the model Mi of the mandibular arch).

A pointer provided with markers detectable by the stereoscopic camera is used.

Figure 6B:
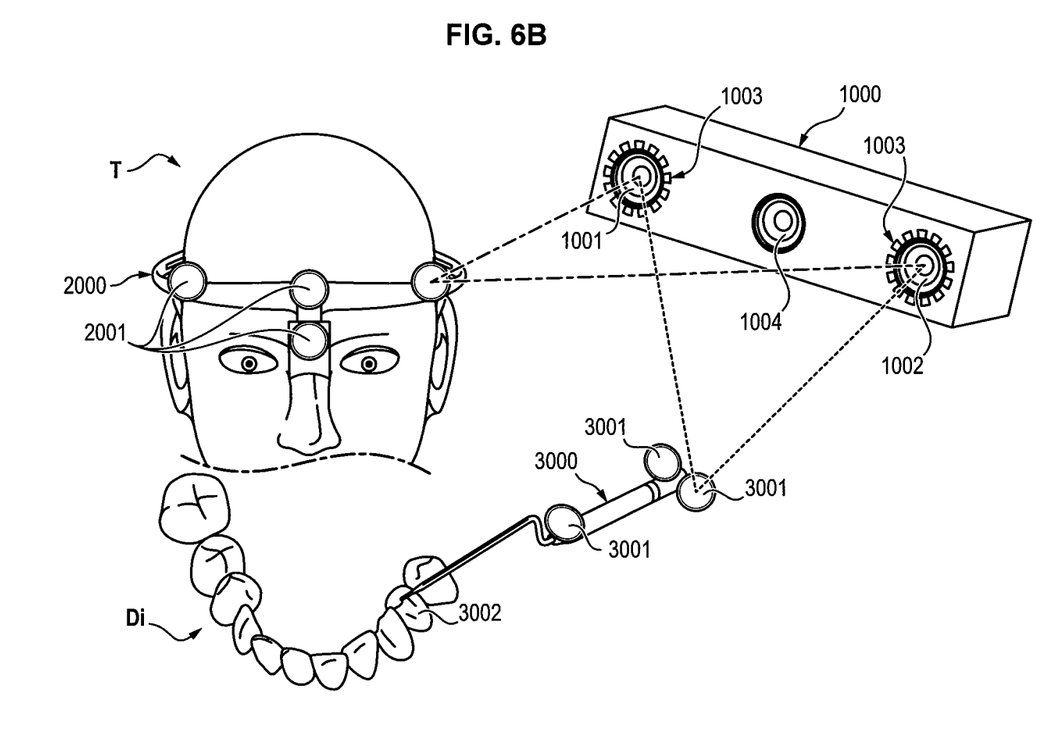

In this step, the practitioner makes sure to place the tip of the pointer precisely in the mouth of the patient on the mandibular arch Di at the same spots as on the virtual model (cf. FIG. 6B).

FIG. 6B illustrates an embodiment of the hardware means of the modeling system.

Said system comprises a stereoscopic camera 1000 having two objectives 1001, 1002. Optionally, the camera 1000 further comprises infrared light emitters 1003 arranged for example around the objectives 1000, 1001. Optionally, the camera 1000 comprises a video-projector 1004 making it possible to project structured light or a laser emitter making it possible to project laser bands on the face of the patient with a view to the modeling described above.

The system further comprises a frontal headset 2000 intended to be placed on the head T of the patient. This frontal headset supports a plurality of markers 2001 visible by the stereoscopic camera 1000. When the camera is provided with infrared emitters 1003, the markers 2001 are advantageously made of a reflective material, the infrared light then serving to increase the visibility of the markers 2001 by the camera 1000. Naturally, the shape of the headset and the number of markers are only illustrated in FIG. 6B for illustrative purposes and those skilled in the art will be able to choose another support and another layout of the markers without going beyond the scope of the present invention. Furthermore, any marker technology visible by the camera may be employed, notably diodes, black and white or color targets or spheres, chips or other reflective objects.

For the embodiment consisting in positioning the dental arches on the 3D model of the face of the patient by pointing, the system further comprises a pointer 3000 bearing markers 3001 visible by the stereoscopic camera 1000. When the camera is provided with infrared emitters 1003, the markers 3001 are advantageously made of a reflective material, the infrared light then serving to enhance the visibility of the markers 3001 by the camera 1000. Naturally, the shape of the pointer and the number of markers are only illustrated in FIG. 6B for indicative purposes and those skilled in the art will be able to choose another shape of pointer and another layout of the markers without going beyond the scope of the present invention. Furthermore, any marker technology visible by the camera may be employed, notably diodes, black and white or color targets or spheres, chips or other reflective objects.

In use, the markers 3001 of the pointer 3000 are detected by the camera 1000.

As soon as the practitioner has positioned the tip 3002 of the pointer on a targeted point, he/she carries out an action aiming to record the position of the end 3002 of the pointer in space. This action may be for example a pressure of a foot on a control pedal, a pressure of a finger on a switch, or instead a masking of the markers by the hand of the practitioner (non-limiting list). At each of these actions, the position of the targeted points is seen by the stereoscopic camera. When the points to be pointed selected on the 3D model have been situated on the dental arch Di and validated thanks to the pointer, the 3D model takes its place with respect to the frame of reference.

Beforehand, the dental arches have been scanned in a known and reproducible meshing occlusion relationship. The tool used is an intrabuccal optical imprint camera. One arch is scanned then the other, as well as a vestibular imprint (on the side) of the teeth while interlocking to know the position of one arch with respect to the other. This operation is known per se and does not as such form part of the invention. Another method could consist in using a table scanner. This scans the plaster models derived from physical-chemical imprints one after the other then in interlocking position. The invention may in fact be implemented with any 3D model of the dental arches generated by commercially available techniques.

Thanks to the prior operation having made it possible to know the situation of the reference planes and axes, the position of the maxillary with respect to the reference plane is thus then deduced. In the same way, the 3D model of the maxillary follows the movements of the head by application of augmented reality or thanks to the use of the aforementioned frontal headset.

Case 2: Detection of Teeth by Facial Recognition

Figure 7A:
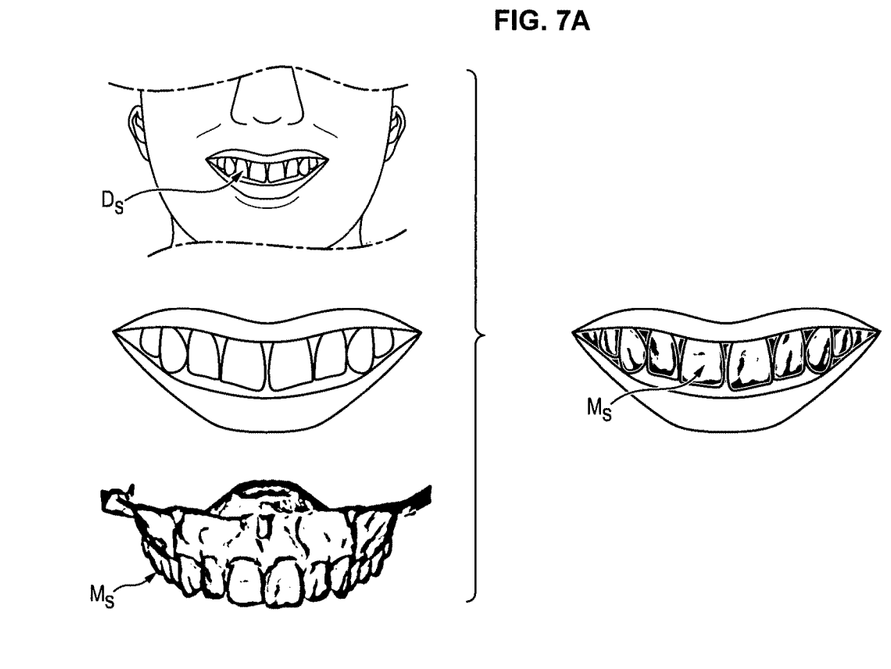
FIG. 7 illustrates the principle of the detection of teeth by facial recognition.

As illustrated in FIGS. 7A and 7B, the stereoscopic camera can visualize, if access to the teeth is allowed by retractors, or during a forced smile, the positioning of the upper dental arch (top view on the left of FIG. 7A, showing the teeth of the maxillary arch Ds). Once the depth map obtained for the visible maxillary teeth or when the characteristic lines of the teeth have been plotted by facial recognition (middle view on the left of FIG. 7A), it is possible to associate on the 3D model of the face or on the video image, the 3D model of this same arch obtained by optical scanner (bottom view on the left of FIG. 7A, showing the 3D model Ms of the maxillary arch).

The registering is done automatically from points characteristic of the teeth thanks to a geometric analysis by plotting the prominent points, corners, contours, transition lines, etc. (right view of FIG. 7A).

The 3D model is then integrated and deformed thanks to a transformation matrix to be registered on the image of the face or on its modeling.

Figure 7B:
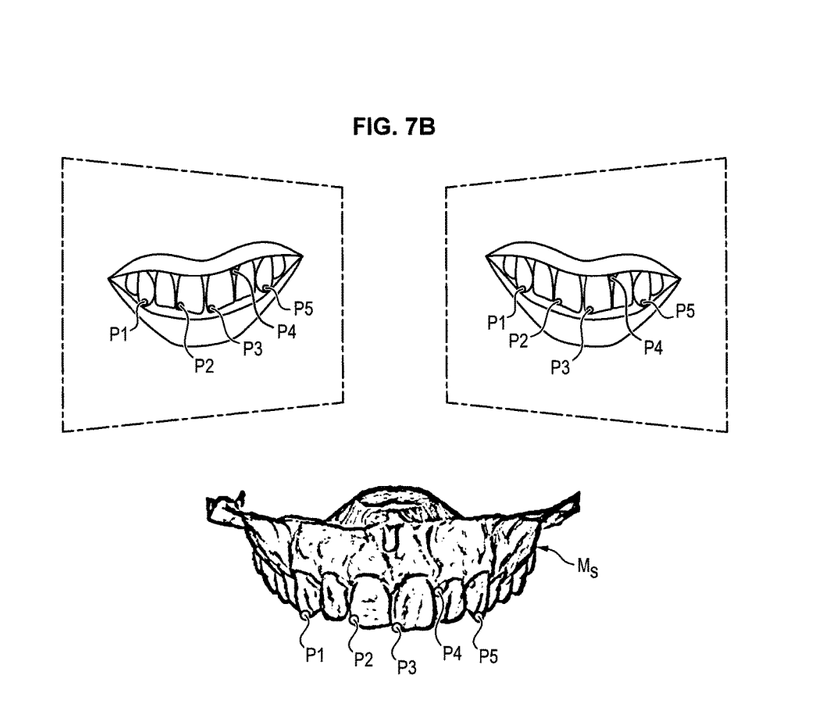

It can be done manually by applying the registering points P1 to P5 (cf. FIG. 7B). on the image or the 3D model of the face as well as on the 3D model of the dental arch.

Once the position of the 3D model found and validated, it is next locked in by the augmented reality technique or by the application of the frontal headset placed on the head of the patient. As are the reference planes, axes and points.

Recording and Studying the Mandibular Kinematics

Figure 8:
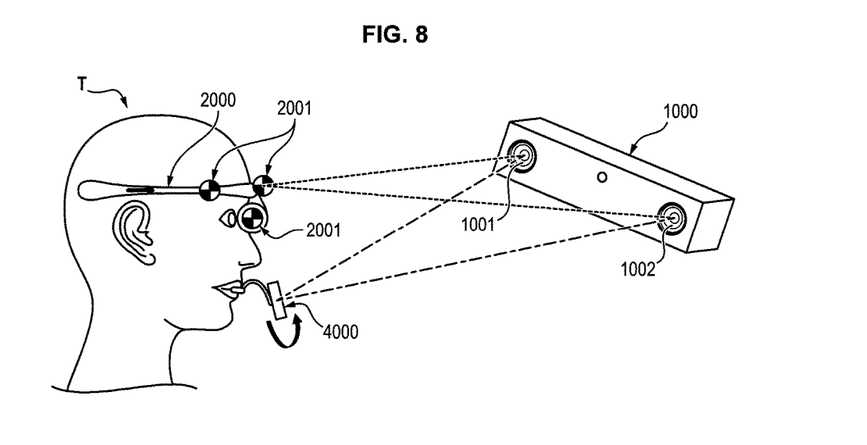
FIG. 8 illustrates the principle of recording the mandibular kinematics of the patient.

As illustrated in FIG. 8, an arch 4000 fixed to the teeth bearing markers detectable by a camera is put in place on the mandible of the patient.

The patient is furthermore also equipped with the aforementioned frontal headset 2000, and bearing markers 2001 detectable by said camera.

Preferably, the stereoscopic camera 1000 used in the preceding steps of the method is used in this step. Thus, a single image acquisition hardware is sufficient to implement the whole of the method, which simplifies the equipment required and limits the cost thereof.

It remains however possible to use any other type of commercially available camera, subject to equipping the fixed arch on the mandible with markers detectable by said camera.

Recording the Kinematics

The static position of the mandibular model with respect to the maxillary (IMR, intermaxillary relationship) has been recorded beforehand in the mouth by an intrabuccal optical camera or at the level of a laboratory table scanner. It is henceforth necessary to know in what way the mandible moves in space. The principle is the same as previously. Markers are placed uniquely on the mandibular teeth.

Here the tracker is composed of diodes followed by the camera. But it may be black and white or colored targets or spheres, chips or other reflective objects. The displacement of the markers of the mandible is monitored by the camera 1000 and does so with respect to the markers 2001 of the forehead. A rigid transformation makes it possible to deduce the movement of the 3D model of the mandibular arch with respect to the 3D maxillary model.

The camera assures the monitoring of the markers placed on the frontal frame of reference 2000 and that of the markers integral with the mandibular arch in movement. The fixation of markers is achieved by means of the arch 4000 or a mouth guard.

The model of the maxillary arch and the reference planes are associated with the animation of the mandible in movement. In the software it is possible to display or to hide each of these elements.

The study of the contacts in dynamic mode is carried out with the same tools as for the study in static mode. In this case, information is obtained on the distribution of interarch conflicts in time and space.

Figure 9:
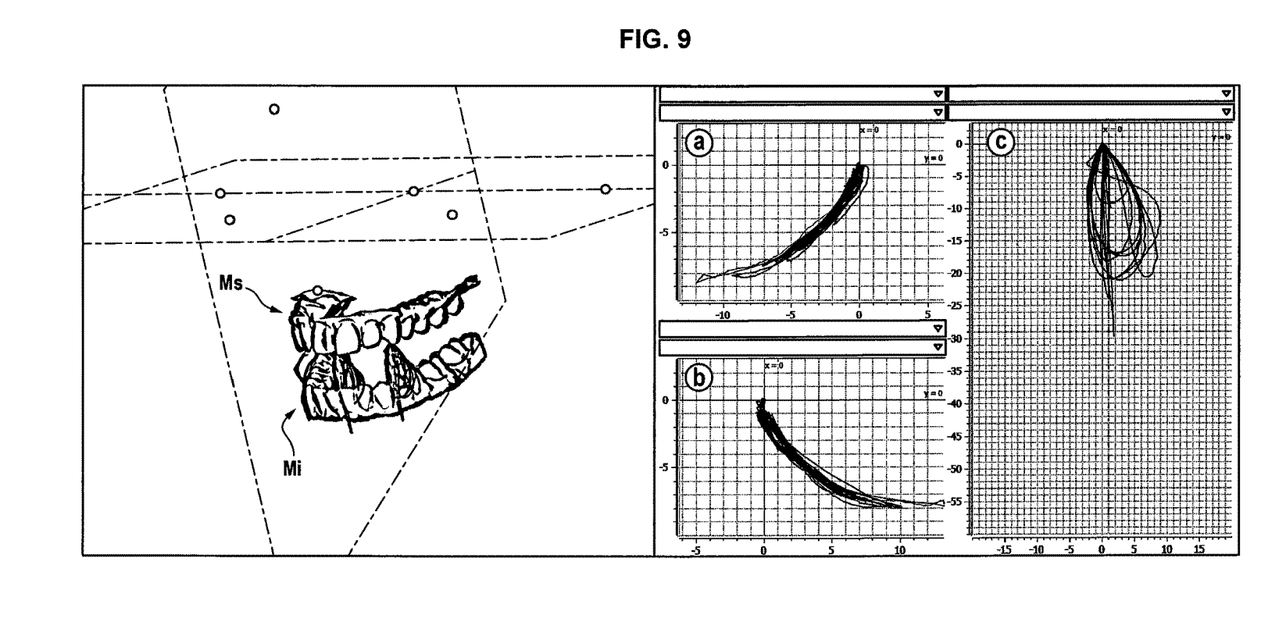
FIG. 9 is a view of the display screen.

FIG. 9 is a view of the display screen showing examples of visualizations obtained. The left part shows the model Ms of the maxillary arch and the model Mi of the mandibular arch with respect to the reference planes of the face of the patient. In the right part, zone a displays the plot of the movement of the left condyle in the sagittal plane, zone b displays the plot of the movement of the right condyle in the sagittal plane and zone c displays the plot of the movement of the dental in the frontal plane.

Localization of the Condylar Point by Kinematic Study

Ideally, the condylar point should correspond to a point of the condylar head which remains immobile during pure rotational movements of the mandible.

This pure rotation is found again during buccal opening in the first 15 to 20 millimeters and in the laterality movements at the level of the pivoting condyles, that is to say located on the side of the displacement of the mandible.

A point being at the least an intersection of two straight lines, it is thus necessary to determine two axes of rotation corresponding to buccal opening and to the right and left laterality movements.

The starting point is the physical law describing the displacement of a solid body in space: the displacement of a rigid body between two points may be described as a rotation around an axis and a translation along said axis.

In the method implemented in the present invention, it is sought firstly to place the axis of rotation corresponding to the opening-closing movement.

This axis, around which the mandibular movement takes place, may be determined mathematically. To this end, three points are firstly chosen on the model of the lower dental arch and create a system of reference coordinates. The axis of rotation is found by resolving automatically by an algorithm the transformation matrix representing the displacement of these three points between the closed mouth and the open mouth position between 15 and 20 mm. To situate the axis of rotation and resolve the transformation matrix, the hypothesis is made that the mandible carries out a pure rotation movement. If not, there are an infinite number of axes of rotation, each with a different translation vector.

The calculation is the same by making the acquisition of the laterality movement and by resolving the transformation matrix representing the displacement of three points placed on the mandibular model between the closed mouth position and the extreme laterality position.

Figure 10A:
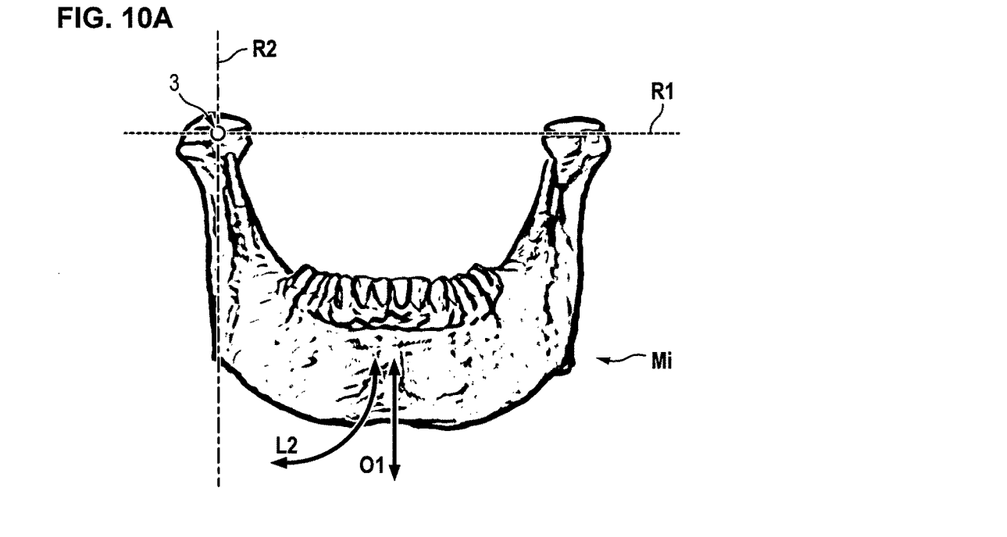
FIGS. 10A and 10B illustrate the principle of localizing the right condylar point by a kinematic study.
Figure 10B:
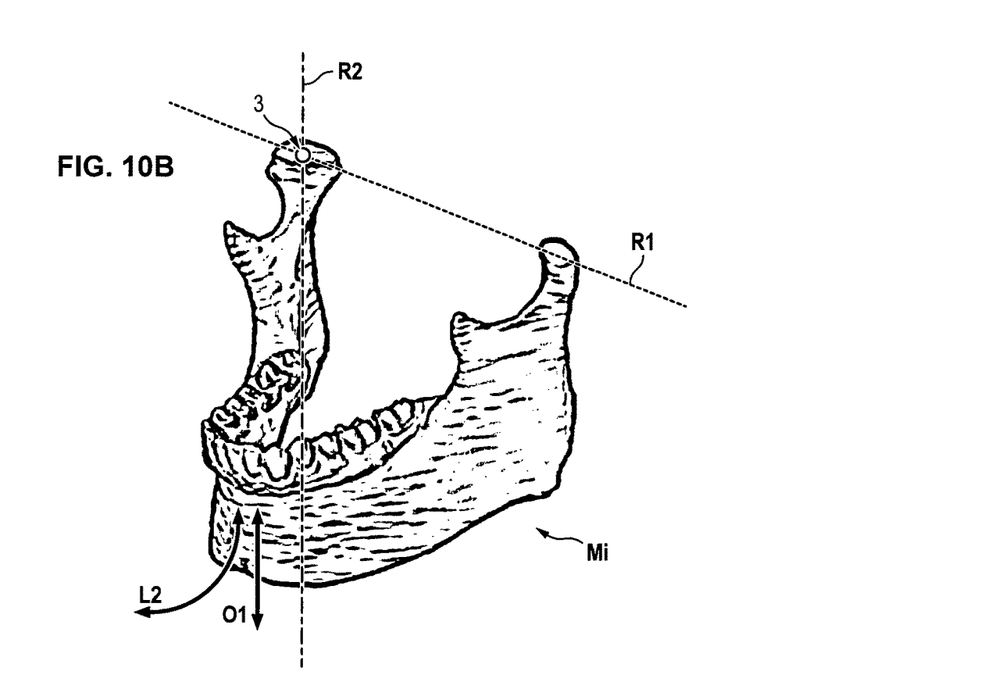

FIGS. 10A and 10B illustrate this principle of localization of the condylar point, respectively on a front view and a side view of the mandible. A focus is made in these figures on the right condylar point 3, which is located at the intersection of the two axes of rotation:
- the axis of rotation R1 that an opening-closing movement of 20 mm of 20 mm amplitude (double arrow O1) is determined,
- the axis of rotation R2 that is obtained by a right laterality movement (double arrow L2).

Protocol Once the Patient is Equipped with the Movement Capturing System

Asking the patient to open and close his/her mouth with a degree of amplitude of 15-20 mm in a repeating manner. To execute this movement, the patient may be guided by the dentist, who may take hold of the chin and guide these movements.

Asking the patient to shift her/her chin as far as possible to the right side and to repeat this movement.

Asking the patient to shift her/her chin as far as possible to the left side and to repeat this movement.

The software displays the right condylar point, which corresponds to the intersection between the right axis of rotation in right laterality with the axis of rotation of the opening-closing.

The software displays the left condylar point, which corresponds to the intersection between the left axis of rotation in left laterality with the axis of rotation of the opening-closing.

Incorporation of Bone Structures

The 3D model of the bone structures is not necessary in the method for placing the dental arches in space and with respect to the facial skeleton.

However, the integration of this model may be interesting for certain applications, notably:

1) to refine the diagnostic examination during the study of the kinematics 2) to make the study of the kinematics more convivial and intuitive 3) to obtain bone volume information and the relationship of the roots of the teeth therewith before the orthodontic treatment and to plan this same treatment 4) to obtain the bone volume information available to anticipate the fitting of dental implants 5) to plan a maxillofacial surgery by displacement of the bone structures according to predetermined reference planes and axes.

Three Methods are Possible:

The first is, from an X-ray tomodensitometric examination, to conduct a 3D reconstruction of the bone volume with the possibility, if necessary, of individualizing the roots. The DICOM file obtained after the examination is next processed by computer, thanks to an algorithm derived from the marching cubes algorithm. The aim is to extract, after thresholding, the corresponding volume of interest. Here the volumes to reconstruct have a density corresponding to the dental tissue or to the bone tissue.

Quite particular care is also taken with the temporomandibular joint to separate the mandible bone from the temporal bone.

In the software, its choice made, these parameters determined, it is possible to obtain automatically a 3D surface rendering of the different structures. A registering is necessary and may be done from teeth that are both visible on the tomodensitometric examination but also on the 3D models of the dental arches coming from the optical scanning.

This technique is to favor in applications 3) and 4) but is applicable for all situations.

A second method is based on the connection of a portable ultrasound device to the computer in order to carry out a 3D ultrasound of the maxillary bones (mandible and maxillary). The ultrasound is based on the emission and the reflection of ultrasound waves as well as the acoustic impedance of a medium, that is to say the capacity of a living tissue to propagate or not an ultrasonic wave (resistance to propagation). Thus, it is by modulating the intensity of these ultrasound waves that information is obtained on the presence at a given spot of a given tissue. The acoustic impedance being known for each tissue of the human body, it is possible to target the bone and to obtain, thanks to the emission of ultrasounds of a suitable power and in several directions, the volume of the bone and to undertake its 3D computer reconstruction.

The 3D models of the dental arches derived from optical scanning are next superimposed by registering on the 3D model obtained by ultrasounds by relying on the shape of the teeth visible on the two examinations.

The two maxillary and mandibular bones are individualized and attached to their corresponding arches, which next makes it possible to apply to them the movements from the motion capture.

The third method is the reverse method of dermoplasty or facial reconstruction. It will be recalled that the dermoplasty method is employed by anthropologists or the forensic police for establishing the portrait of a deceased person. It consists in affixing a volume of material on a dry skull in order to reconstruct the volume of the face, these thicknesses of materials corresponding to the layer of the different masticatory and platysma muscles as well as fat and the dermis, and which are relatively constant in hominids.

The method implemented in the invention is the reverse method, known as "BONE MORPHING". It consists in deducing the underlying bone volume from the 3D surface model of the face of the patient. The mandibular bone is then fused to its corresponding dental arch and set in motion.

This method is more particularly recommended for applications 1) and 2).

Applications

By making it possible to integrate the different determinants of the occlusion, the method as described above makes possible optimal therapeutic conduct in numerous clinical situations, notably the appraisals and clinical treatments developed above.

Occlusal Analysis

Occlusal analysis is the study of the distribution of the teeth on the dental arches, the manner in which the teeth of the two arches engage together in static mode and also in dynamic mode. To this end, it is thus necessary to have references specific to each patient. In this case, the information items to obtain are planes characteristic of the face to deduce therefrom the correct positioning and the correct orientation of the anterior and posterior teeth within the facial skeleton, in order to situate the ideal occlusal plane thanks to an occlusal cap deduced by computer. It is also necessary to quantify and qualify the dental contacts in static mode and in dynamic mode (mastication, propulsion, laterality) as well as the motility of the temporomandibular joint. The acquisition and the reproduction of the movement of the individual, which are required for this purpose, are permitted by a recording directly on the patient.

Mouth Guard/Interocclusal Orthosis

A mouth guard is a device, generally made of hard material, fixed on a temporary basis on the maxillary or mandibular arch and having the aim of modifying the intermaxillary relationships in a reversible manner. In this case, it is important to manage the acquisition of the movement. The comparison between the displacement of the TMJ and the dental arches will make it possible to choose digitally the best inter-maxillary relationship (positioning of the mandibular arch with respect to the maxillary arch).

Dental Prosthesis

This consists in restoring or replacing teeth thanks to the fixation in the mouth of prosthetic devices. The organization (the placement) of the different restorations will be guided with respect to the occlusion plane in the form of occlusal cap deduced by computer. The occlusal morphology, the upper part of the tooth, is designed to be integrated in the mandibular kinematics of the patient. It is important to manage the acquisition of the movement. The acquisition of the 3D model of the face is also useful for the aesthetic arrangement of the teeth in the anterior sector.

Dentofacial Orthopedics/Orthodontics

This involves the correction of the incorrect positions of the jaws (DFO: dento-facial orthopedics) or the teeth (orthodontics) in order to optimize the occlusion (intercuspidation), as well as the development of the bony bases with a functional and aesthetic aim. This is done with fixed or removable appliances. Before the digital design of the orthodontic appliance the result may be planned thanks to a simulation of dental displacements within the bony bases. The positioning and the orientation of the arches with respect to the facial skeleton are searched for, the quality of intercuspidation in static mode and in dynamic mode before, during and after the treatment are recorded. The 3D reconstruction of the bone of the maxillaries and the volume of the roots from the X-ray tomodensitometric examination is also useful for anticipating the positioning at the end of the treatment of the roots with respect to each other as well as with respect to the available surrounding bone. The aesthetic project of the orthodontic treatment is implemented by obtaining the digital 3D face of the patient.

Maxillofacial Surgery

In severe cases of dysmorphoses, it is sometimes necessary to resort jointly to a maxillofacial surgery intervention to complete the orthodontic treatment. The maxillary and or mandibular displacements are then carried out according to a mandibular-cranial relationship recorded and conserved and along a reference plane (the axis-orbital plane neighboring the Frankfurt plane).

Finally, it goes without saying that the examples that have been given are only particular illustrations that are in no way limiting with regard to the fields of application of the invention.

REFERENCES

WO 2013/030511

The invention claimed is:
1. A method for modeling the mandibular kinematics of a patient, comprising:
   acquiring at least one stereoscopic image of the face of the patient by means of a stereoscopic camera,
   constructing, from said stereoscopic image, a three-dimensional surface model of the face of the patient,
   identifying characteristic elements of the face of the patient on said stereoscopic image or on said three-dimensional surface model of the face of the patient,
   from said characteristic elements, determining, on said stereoscopic image, respectively said three-dimensional surface model of the face of the patient, reference points, axes and planes of the face of the patient,
   obtaining a three-dimensional model of the maxillary dental arch and a three-dimensional model of the mandibular dental arch of the patient,
   registering the three-dimensional models of the dental arches with respect to the reference planes of the three-dimensional surface model of the patient,
   recording the mandibular kinematics of the patient,
       applying said recorded mandibular kinematics to the three-dimensional models of the registered dental arches, so as to animate said three-dimensional models.

2. The method according to claim 1, wherein the stereoscopic image of the face of the patient is a color image and in that a texture based on said image is applied to the three-dimensional surface model.

3. The method according to claim 1, wherein the stereoscopic image of the face of the patient is a black and white image of the face of the patient and wherein after constructing the three-dimensional surface model from said image, a color image of the face of the patient is imported and a texture is applied to said model from said imported color image.

4. The method according to claim 1, further comprising the display in real time, on a screen, of a video image of the face of the patient acquired by the stereoscopic camera and reference axes and planes of the face of said patient.

5. The method according to claim 1, wherein the step of registering the three-dimensional models of the dental arches with respect to the reference planes of the patient comprises:
generating a plurality of points on the dental arches in the three-dimensional surface model of the face,
pointing said points in the mouth of the patient by means of a pointer bearing markers detectable by the stereoscopic camera,
detecting said markers by the stereoscopic camera while pointing each point and determining each point in the frame of reference of the camera,
matching the points between the frame of reference of the camera and the three-dimensional surface model.

6. The method according to claim 5, wherein while pointing the points in the mouth of the patient, the head of the patient is equipped with a plurality of markers visible by the stereoscopic camera.

7. The method according to claim 1, wherein the step of registering the three-dimensional models of the dental arches with the three-dimensional surface model of the face comprises:
obtaining a stereoscopic image of the face of the patient on which appear at least three teeth of the maxillary dental arch of the patient,
detecting said teeth by a facial recognition method,
matching said teeth on the three-dimensional surface model of the patient and on the model of the maxillary dental arch.

8. The method according to claim 1, further comprising constructing a three-dimensional model of the bone structure of the face of the patient.

9. The method according to claim 8, wherein said construction is carried out from a tomodensitometric image of the head of the patient.

10. The method according to claim 8, wherein said construction is carried out from an ultrasound image of the bones of the mandible and the maxillary.

11. The method according to claim 1, wherein said construction is carried out by a "BONE MORPHINE" technique from the three-dimensional surface model of the face of the patient.

12. The method according to claim 1, wherein to register the mandibular kinematics of the patient, a set of markers detectable by the stereoscopic camera is fixed on the head of the patient and said mandibular kinematics are recorded by means of said stereoscopic camera.

13. The method according to claim 1, wherein infrared light is emitted towards the face of the patient by means of infrared emitters arranged on the stereoscopic camera.

14. The method according to claim 1, wherein light structured by means of a projector arranged on the stereoscopic camera is projected onto the face of the patient.

15. A system for modeling the mandibular kinematics of a patient for the implementation of the method according to claim 1, comprising:
a processor,
a memory coupled to the processor,
a display screen coupled to the processor for displaying data calculated by the processor,
a stereoscopic camera coupled to the processor for providing stereoscopic images of the face of the patient,
a set of markers detectable by the stereoscopic camera, comprising a device for fixing said set to the head of the patient, such as a headset.

16. A method for modeling the mandibular kinematics of a patient, comprising:
acquiring at least one stereoscopic image of the face of the patient by means of a stereoscopic camera,
constructing, from said stereoscopic image, a three-dimensional surface model of the face of the patient,
identifying characteristic elements of the face of the patient on said stereoscopic image or on said three-dimensional surface model of the face of the patient,
from said characteristic elements, determining, on said stereoscopic image, respectively said three-dimensional surface model of the face of the patient, reference points, axes and planes of the face of the patient,
obtaining a three-dimensional model of the maxillary dental arch and a three-dimensional model of the mandibular dental arch of the patient,
registering the three-dimensional models of the dental arches with respect to the reference planes of the three-dimensional surface model of the patient,
recording the mandibular kinematics of the patient, wherein a set of markers detectable by the stereoscopic camera is fixed on the head of the patient and said mandibular kinematics are recorded by means of the stereoscopic camera,
applying said recorded mandibular kinematics to the three-dimensional models of the registered dental arches, so as to animate said three-dimensional models.

17. The method according to claim 16, wherein the step of registering the three-dimensional models of the dental arches with respect to the reference planes of the patient comprises:
generating a plurality of points on the dental arches in the three-dimensional surface model of the face,
pointing said points in the mouth of the patient by means of a pointer bearing markers detectable by the stereoscopic camera,
detecting said markers by the stereoscopic camera while pointing each point and determining each point in the frame of reference of the camera,
matching the points between the frame of reference of the camera and the three-dimensional surface model.

* * * * *